United States Patent
Suzuki

(10) Patent No.: US 6,599,010 B1
(45) Date of Patent: Jul. 29, 2003

(54) THERMO-MECHANICAL ANALYZER

(75) Inventor: Tetsuo Suzuki, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 09/517,673

(22) Filed: Mar. 2, 2000

(30) Foreign Application Priority Data

Mar. 3, 1999 (JP) ............................................. 11-055488

(51) Int. Cl.$^7$ ................................................ G01N 3/00
(52) U.S. Cl. ........................... 374/46; 374/49; 374/51; 73/818; 73/826
(58) Field of Search ............................. 374/46, 49, 50, 374/51; 73/818, 826, 856

(56) References Cited

U.S. PATENT DOCUMENTS

| | | | |
|---|---|---|---|
| 3,589,167 A | * | 6/1971 | Hill ............................ 336/136 |
| 4,603,588 A | | 8/1986 | Niermann et al. |
| 5,370,457 A | * | 12/1994 | Iizuka ........................... 374/51 |
| 5,452,614 A | * | 9/1995 | Kato et al. .................... 73/789 |
| 5,667,306 A | * | 9/1997 | Montreuil et al. ........... 374/208 |
| 5,703,302 A | * | 12/1997 | Hasler et al. ................ 73/865.8 |
| 6,146,013 A | * | 11/2000 | Huetter et al. ................. 374/46 |

FOREIGN PATENT DOCUMENTS

DE     3906490     9/1989

* cited by examiner

Primary Examiner—Diego Gutierrez
Assistant Examiner—Lydia M. De Jesús
(74) Attorney, Agent, or Firm—Hogan & Hartson, LLP

(57) ABSTRACT

A slit for probe-changing is provided above an opening for changing a test piece on a side of a test piece tube for installing test pieces. Probes are then taken out and inserted via this slit. Probes can therefore be changed without taking out the test piece tube or a thermocouple. This improves work efficiency and means that the work can be carried out in a confined space because the probes are pulled forward towards an operator and inserted in the opposite direction.

11 Claims, 5 Drawing Sheets

THERMO-MECHANICAL ANALYZER

BACKGROUND OF THE INVENTION

The present invention relates to a thermo-mechanical analyzer.

FIG. 5 is a cross-sectional view of a configuration of a thermo-mechanical analyzer and FIG. 6 is an external view showing a configuration of a sample mounting section.

A test piece 10 is placed on the closed bottom of a cylindrical test piece tube 11, and is subjected to arbitrary loads by a probe 2. A heating furnace 18 is provided about the bottom of the test piece tube 11. The heating furnace 18 is temperature-controlled by a temperature controller (not shown), in order to control the temperature of the test piece 10. The heating furnace 18 can be moved up and down by a moving mechanism (not shown).

The probe 2 is in contact with the test piece 10 at a lower part, is fastened to a probe coupling 12 at an upper part, and is connected to an auxiliary probe 14 using connecting means 13. The auxiliary probe 14 is fixed to a core 15 of a magnetic material and an auxiliary probe 16, respectively. The probe 2 is movable while connected with the probe coupling 12, the auxiliary probe 14, the core 15 and the auxiliary probe 16. The auxiliary probe 16 and so on are supported above the probe 2 by a spring member, balancing mechanism or the like (not shown). The probe 2 is therefore capable of movement in a vertical direction but movement in other directions is restricted.

The test piece tube 11 is fastened to a test piece tube holder 20. The test piece tube holder 20 is then supported by a test piece tube support member 21 using screws. The test piece tube support member 21 is supported at two vertical shafts 24 standing on a base 19 via shaft holders 23. The test piece tube support member 21 can be moved vertically in parallel with the base 19 by a guide screw 25 and a motor 26.

A force generator 17 comprises a coil 17a and a magnet 17b. This force generator can apply an arbitrary load to the test piece 10 via the probe 2 as a result of the mutual action of the coil 17a and magnet 17b fixed to the auxiliary probe 16.

Deformation of the test piece 10 due to heat from the heating furnace 18 or changing load from the force generator 17 is detected by a differential transformer 22 as relative positional changes of the test piece tube 11 and the probe 2. A signal is inputted to a detection circuit (not shown). The differential transformer 22 is fixed to the shafts 24 and a differential transformer support 27, so as to be indirectly fixed to the base 19.

A thermocouple 29 for measuring temperature of the test piece 10 is protected by an insulating tube 30 and extends outwards from the vicinity of the test piece 10 via a hole 20a of the test piece tube holder 20. The thermocouple 29 extending out of the test piece tube 11 is covered by a flexible insulating tube 31 and is connected to a temperature measuring circuit (not shown).

Methods of applying a load to bring about compression, expansion, bending and stretching etc., for this thermo-mechanical analyzer change depending on the shape of the test piece and the objectives of the measurements, and probes are therefore used with this in mind. Operativity when changing probes is therefore one factor influencing the efficiency of measuring operations as a whole.

A test tube and a probe are made of materials which are resistant to heat in a measuring temperature range and have a small expansion coefficient, or existing materials (for example, molten quartz or sintered aluminum etc.). On the other hand, members such as the test piece tube holder 20 and the probe coupling 12 shown in FIG. 5 are made of metal materials etc. Such metal materials are positioned as far as possible above the heating furnace in order to prevent expansion during high temperature measurements. The test piece tube and the upper end of the probe are aligned, and the length of the metal members are made equal in order to offset changes caused by expansion. As a result, the probe connecting means is above the upper end part of the test piece tube. The probe is preferably as long as possible, so that the differential transformer and the force generator may not be influenced by heat from the heating furnaces.

In order to change the probe, there is a method where a probe is taken out from the lower side of the apparatus and a method where the test piece tube is taken out. These methods involve the trouble of dismantling the test piece tube and this makes the operation complex because it is also then necessary to dismantle the thermocouple for measuring the temperature of the test piece that is inside the test piece tube together with the test piece tube. However, if just the test piece tube is removed without extracting the thermocouple in order to avoid complicating the operation, there is a possibility that the relative positions of the end of the thermocouple and the test piece tube will change after reassembly, which is a factor in causing poor reproduction of temperature measurements.

Alternatively, a probe might be removed downward from the apparatus via an opening in the side of the test piece tube. However, the opening is of a size just for changing the test pieces and is made as small as possible in order to guarantee the mechanical strength of the test piece tube. On the other hand, it is necessary to make the length of the probe of a length appropriate for the configuration of the apparatus, as described above, and this length is therefore long compared to the length of the opening for changing test pieces. Therefore, the probe cannot be removed via the opening for changing test pieces. Further, if a hole for probe extraction that is separate to the opening for test piece changing is provided in the bottom of a test piece tube, a space longer than the length of the probe should be maintained at the lower part of a thermo-mechanical analyzer, and this will impose design restrictions. The device therefore has to be made larger than is necessary and this causes problems regarding device installation.

On the other hand, when extracting the probe upward from the apparatus, it is necessary to draw the probe up to a height greater than the height of the apparatus. The height of the thermo-mechanical analyzer and the installation table, together with the length of the probe itself, therefore often become greater than the height of an operator, which has the disadvantage of making this operation difficult to perform.

SUMMARY OF THE INVENTION

A small slit sufficient for removing a probe downwards is provided in the side of the lower part of a test piece tube for installing test pieces. The probe is then removed and inserted via this slit-shaped opening. Probes can therefore be changed in confined spaces without removing the test piece tube.

Figure 1A:
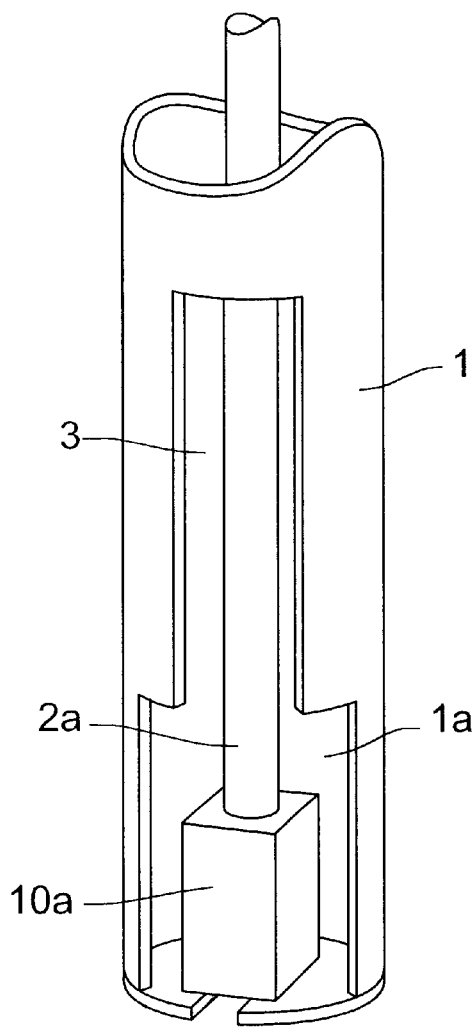
FIG. 1(a) and FIG. 1(b) are external views showing a sample tube, probes and test pieces of the embodiment of the present invention.

KEY TO THE REFERENCE NUMERALS 1 test piece tube
2 probe
2a probe for compression and expansion
2b probe for stretching
3 slit
4a chock
4b chock
10 test piece
10a block-shaped test piece
10b film-shaped test piece
11 test piece tube
12 probe coupling
13 connecting means
14 auxiliary probe
15 core
16 auxiliary probe
17 force generator
17a coil
17b magnet
18 heating furnace
19 base
19a hole
20 test piece tube holder
20a hole
21 test piece tube support member
22 differential transformer
23 shaft holder
24 shaft
25 guide screw
26 motor
27 differential transformer support
28 force generator support member
29 thermocouple
30 insulating tube
31 insulating tube

DETAILED DESCRIPTION OF THE INVENTION

Figure 1B:
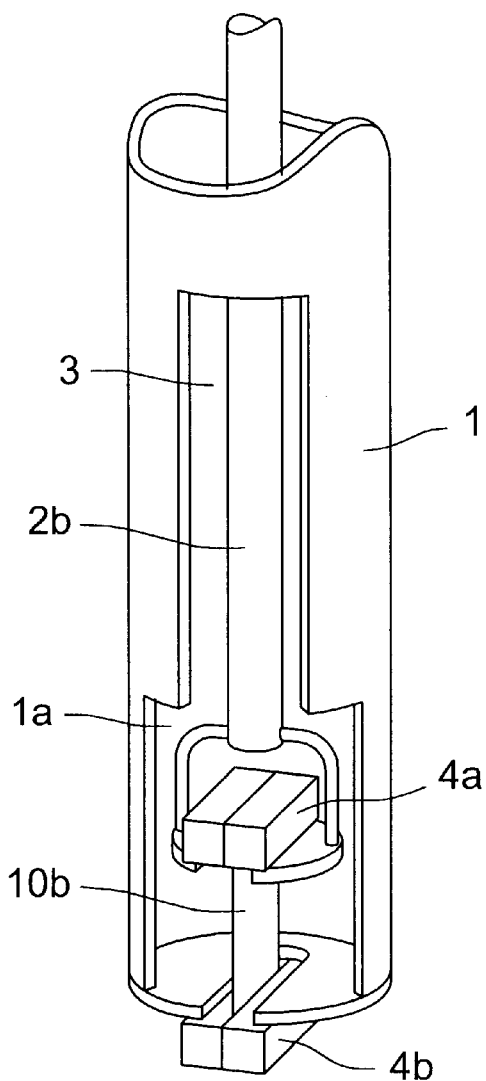
Figure 5:
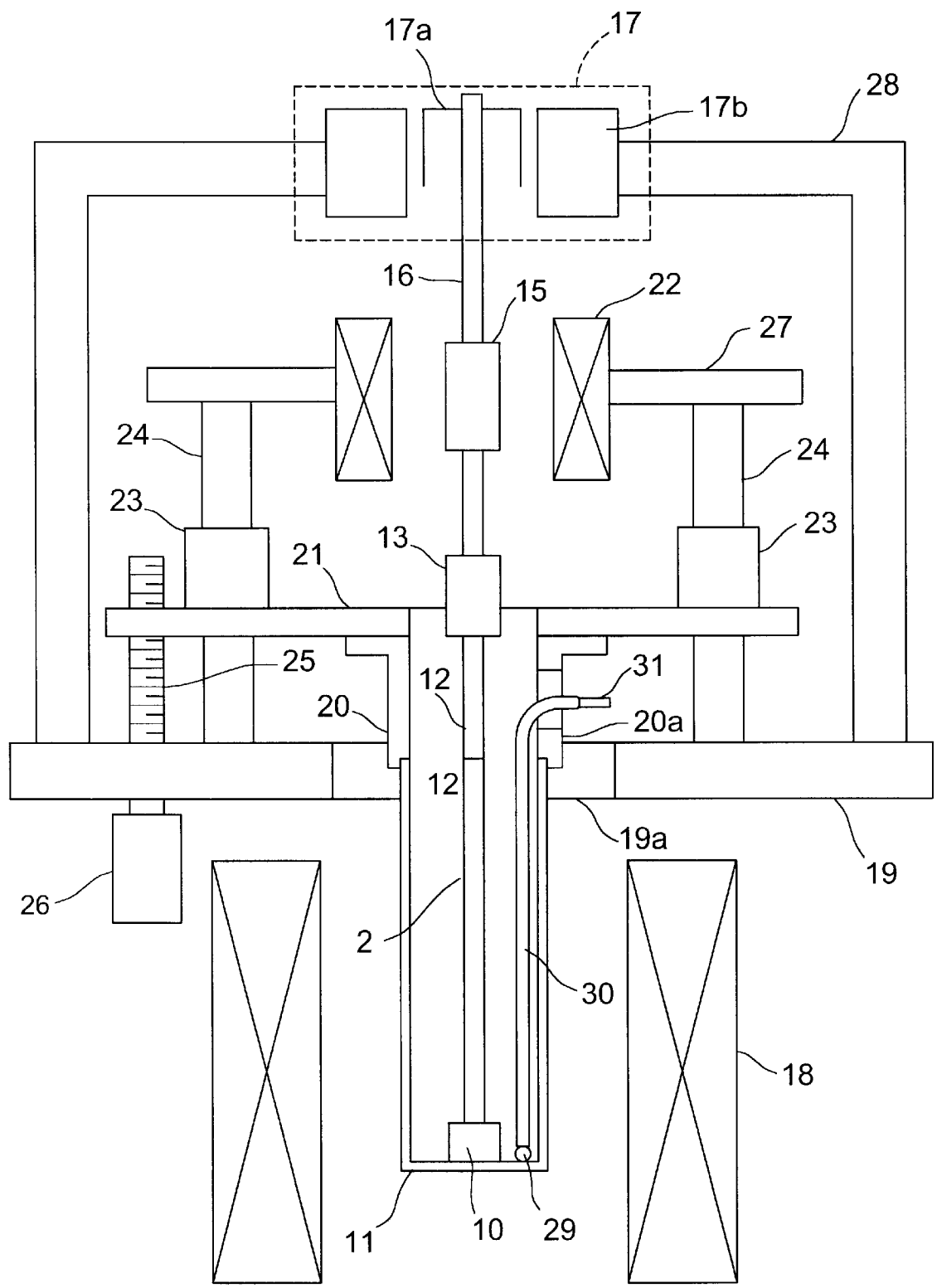
FIG. 5 is a cross-section showing a configuration of a thermo-mechanical analyzer.
Figure 6:
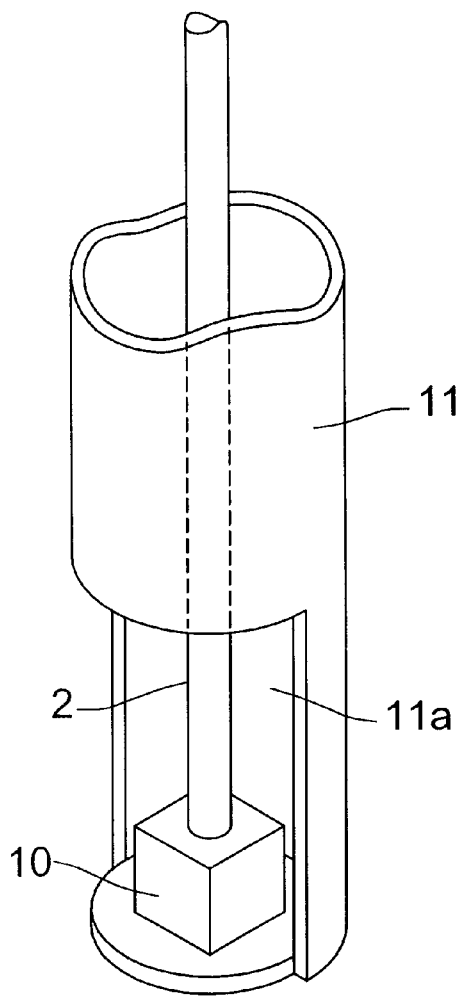
FIG. 6 is an external view showing a test piece tube, probe and test piece of a related example.

The following is a description of the present invention based on an embodiment of a thermo-mechanical analyzer. FIG. 1a and FIG. 1b are external views showing a test piece installation section of a thermo-mechanical analyzer of the present invention. Components other than the test piece installation section are the same as those shown in FIG. 5 for the related example.

FIG. 1a is an external view of a test piece installation section for measuring a block-shaped test piece 10a in compression and expansion modes. The test piece 10a is inserted through an opening 1a provided in the side of the lower part of the closed-ended tube 1 and is arranged on the bottom of the test piece tube 1. A probe 2a for compression and expansion is housed within the test piece tube 1 and has its lower part connected to the upper end of the test piece 10a. FIG. 1b shows an external view of a test piece installation section for measuring a film-shaped test piece 10b in stretching mode. The film-shaped test piece 10b is grasped by chocks 4a and 4b, with the chock 4a being installed at the probe 2b and the chock 4b being installed at the test piece tube 1. The opening 1a for changing test pieces is provided in the test piece tube 1, with a slit 3 provided above the opening 1a. This slit 3 at the upper end of the opening 1a is utilized in extraction and insertion when the probes 2a and 2b etc. are changed. The slit 3 therefore has the necessary width and length required for changing the probes 2a and 2b. The probes 2a and 2b apply arbitrary loads generated by the force generator 17 to the test pieces 10a and 10b, as described for the related art. The test piece tube 1 therefore has mechanical strength to bear this load. The dimensions of the slit 3 are determined on the condition that the probes 2a and 2b can be removed or inserted without loss of mechanical strength of the test piece tube 1. The slit 3, according to the present invention, is independant from the opening 1a for changing the test pieces 10a and 10b. The dimensions of the slit 3 are therefore an important factor.

Figure 2:
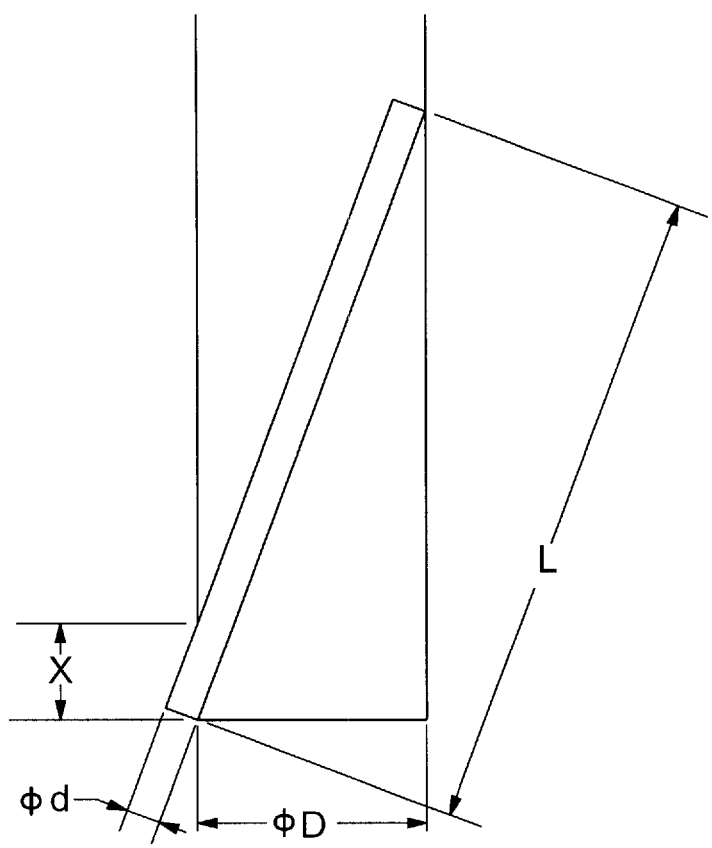
FIG. 2 is a reference view schematically showing cross-sections of a test piece tube and probe, and showing the relationship between each dimension.

Specifically, when the test piece 10a has a maximum height of 20 mm and a maximum diameter of 8 mm, a required height of approximately 22 m and width of approximately 10 mm are sufficient for the opening 1a. It is, however, necessary for the slit 3 to satisfy the dimensions expressed by the following conditional equation, as can be discerned from FIG. 2.

Length of slit $3(X)$:$X > L \times \phi d/\phi D$

Width of slit $3(W)$:$W > \phi d$ where;

L; Length of the probe 2a $\phi d$; Outer diameter of probe 2a $\phi D$; inner diameter of test piece tube 1

In this embodiment, the length of the probe 2a is 200 mm and the outer diameter is 4 mm, and the inner diameter of the test piece tube 1 is 6 mm. In this case, the length of the slit 3 has to be longer than 50 mm and the width has to be broader than 4 mm. On the other hand, there are also probes whose end is larger than other portions, and whose outer diameter is not constant, as with the probe 2b. In that case, the outer diameter of the larger end has to be considered as $\phi d$. As a plurality of probes such as the probes 2a and 2b are prepared in accordance with the shapes of test piece and objectives of the measurements, the dimensions of the slit 3 are set taking into consideration the possibility of changing all kinds of probes, and in this embodiment a slit of length 60 mm and width 6 mm is provided.

The slit 3 can be provided anywhere on the side of the test piece tube providing that no problems occur due to interference etc. with other members of the apparatus at the time of extraction and insertion of the probes 2a and 2b. The slit 3 can also be positioned separately from the opening 1a. In this embodiment, the opening 1a and the slit 3 are constructed taking into consideration ease of operation and are therefore set positioned at the same side so as to face the side of the operator.

The following is a description of a method for extracting the probes 2a and 2b. First, as a setting for the main body of the apparatus, the heating furnace 18 positioned about the bottom of the test piece tube 1 is moved to a lower end position by the moving mechanism so that the test piece tube 1 is exposed from the heating furnace and the test pieces 10a and 10b are removed from the work piece tube 1. In this state, tweezers etc. are inserted into the opening 1a at the lower part of the test piece tube 1, the lower ends of the probes 2a and 2b etc. are fixed, and the connecting means 13 is taken out and isolated from the main body of the apparatus.

Figure 7:
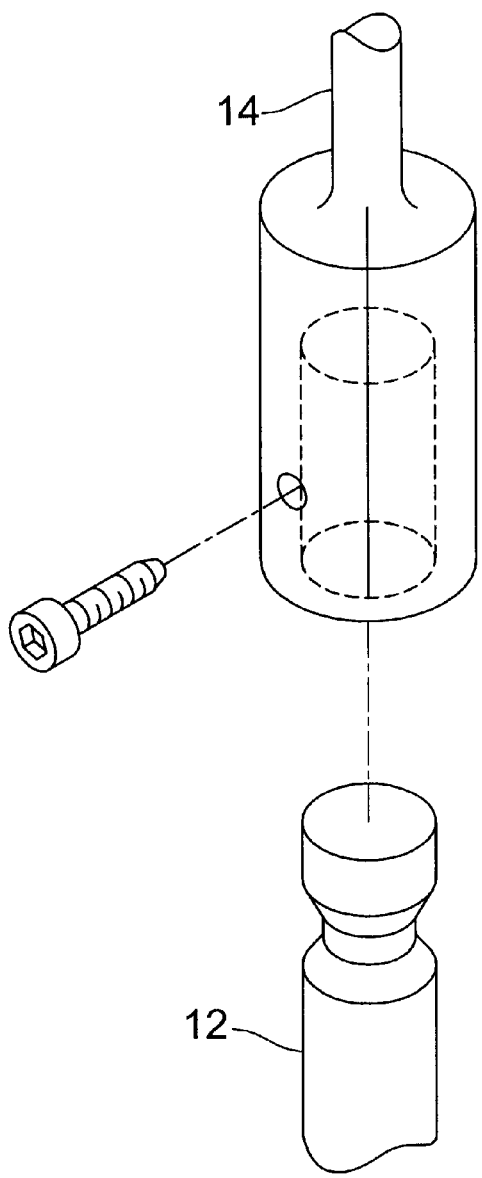
FIG. 7 is an external view showing means for connecting a probe and a main body of an apparatus.

As shown in FIG. 7, the connecting means 13 of this embodiment is such that the probe coupling 12, which has a V-shaped channel at the outer periphery of its upper end, is inserted into the auxiliary probe 14, which has a cylindrical lower end. A screw having the same shape as the V-shaped channel and having a convex tip is then screwed in through a hole in the side of the auxiliary probe 14, the V-shaped channel of the probe coupling 12 and the end of the screw coincide so as to bring about fixing, with loosening then bringing about separation.

Figure 3:
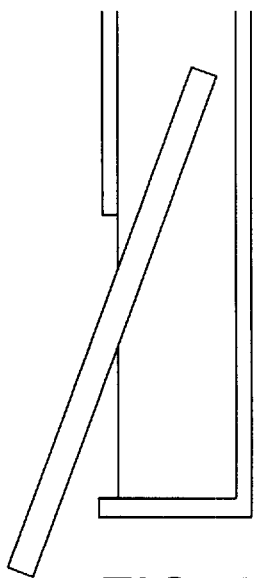
FIG. 3 is a cross-section showing one procedure for changing a probe in the embodiment of the present invention.

The lower end of the probe 2a or 2b separated from the above connected state is fixed using tweezers etc., shifted towards the opening, and moved temporarily downwards, as shown in FIG. 3. The probe 2a or 2b is then drawn towards the operator along the orbit shown by the arrow A in FIG. 4. Insertion in the reverse order is also possible. It is therefore possible to change the probes 2a or 2b etc. without removing the test piece tube and without withdrawing the probes 2a or 2b upward, as in the related art.

Figure 4:
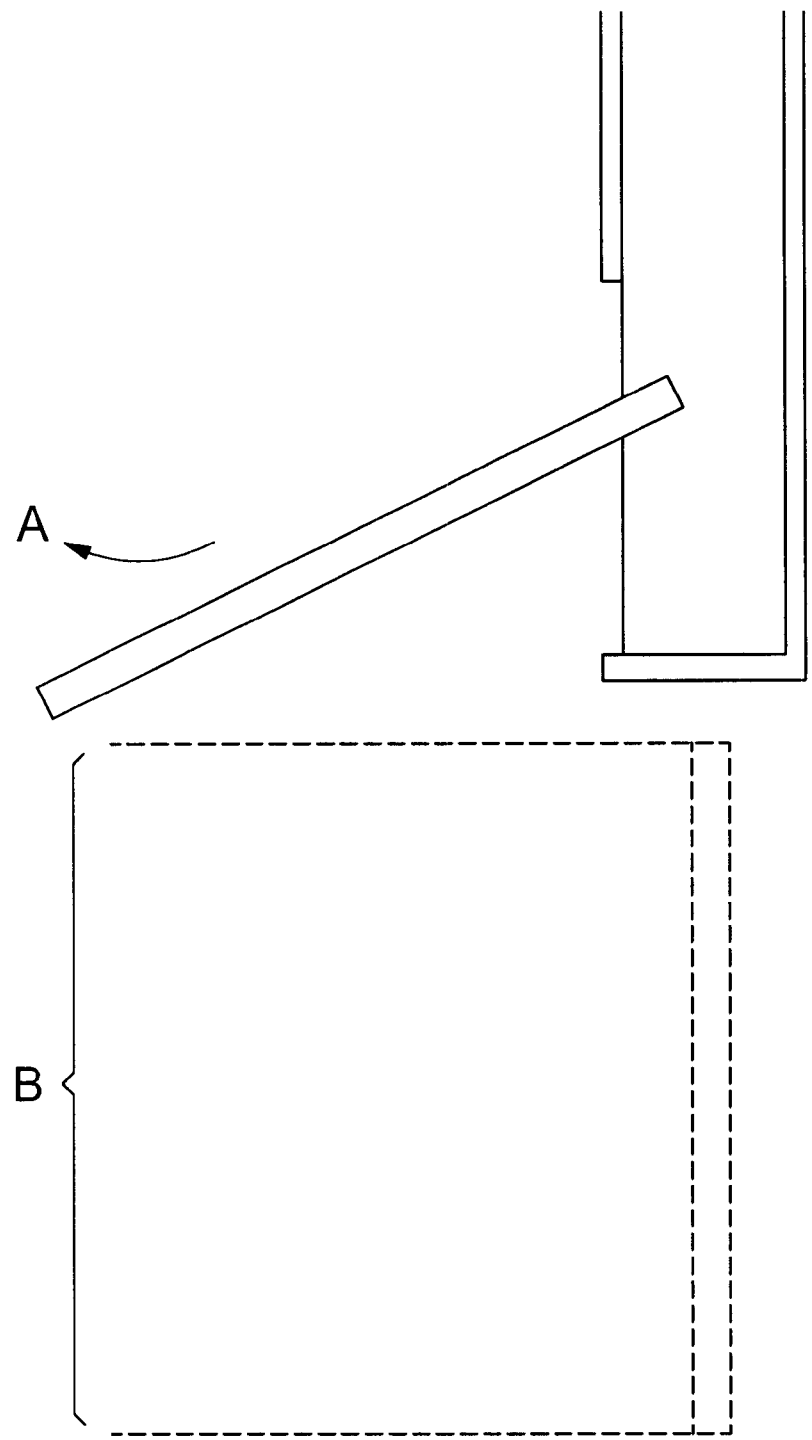
FIG. 4 is a further cross-section showing another procedure for changing a probe in the embodiment of the present invention.

The probe 2a or 2b is changed while still joined to the probe coupling 12. The probe 2a or 2b is fastened to the probe coupling 12 beforehand. Various types of combined probe and probe couplings are available for measurements. The region B shown in FIG. 4 shows the length required in order to extract the probes 2a or 2b to directly below the test piece tube 1. However, this region is not required in this embodiment, and this embodiment can be carried out in a confined space, i.e. there are few limitations put on the dimensions of the apparatus when this embodiment is employed.

With the thermo-mechanical analyzer of the present invention, a probe can be changed by the user without complex operations such as the extraction of a test piece tube and thermocouple and pulling the probe upwards. This remarkably improves the operation of the analyzer, and makes the overall measuring operation more efficient due to the time taken for changing a probe being shortened. Further, as the probe is withdrawn downwards and forward without removing the test piece tube or thermocouple to change the probe, the danger of low reproduction of temperature measurements is avoided, and measurement results become more reliable. It is not necessary to make more space than necessary at the lower part of the apparatus, which makes the apparatus smaller.

What is claimed is:

1. A holder for a test piece in a thermo-mechanical analyzer, the holder comprising:

a rigid elongate probe operable to apply mechanical force to the test piece; and an elongate test piece tube including structure defining an interior space configured to accommodate within it the test piece and the rigid elongate probe;

wherein the test piece tube includes structure defining an opening through an elongate side surface of the test piece tube; and wherein the opening is of a size and shape sufficient to allow the removal of the rigid probe from the test piece tube through the opening.

2. The test piece holder of claim 1, wherein the opening has a width greater than an outer diameter of the probe.

3. The test piece holder of claim 2, wherein the length of the opening is greater than the length of the probe multiplied by the ratio of the outer diameter of the probe to an inner diameter of the test piece tube.

4. The test piece holder of claim 1, wherein the opening is of a size and shape sufficient to allow the removal of the test piece through the opening.

5. The test piece holder of claim 1:

wherein the elongate test piece tube defines a long axis;

wherein the opening comprises a slit substantially parallel to the long axis of the test tube piece; and wherein the opening is of a length less than a length of the rigid elongate probe.

6. A thermo-mechanical analyzer comprising:

a rigid elongate probe operable to apply mechanical force to a test piece;

a force generator operable to apply a mechanical force to the rigid elongate probe and thereby to the test piece;

an elongate test piece tube including structure defining an interior space configured to accommodate within it the test piece and the rigid elongate probe; and a temperature sensor operable to measure the temperature of the test piece;

wherein the test piece tube includes structure defining an opening through an elongate side surface of the test piece tube; and wherein the opening is of a size and shape sufficient to allow the removal of the rigid probe from the test piece tube through the opening.

7. The thermo-mechanical analyzer of claim 6, wherein the opening has a width greater than an outer diameter of the probe.

8. The thermo-mechanical analyzer of claim 7, wherein the length of the opening is greater than the length of the probe multiplied by the ratio of the outer diameter of the probe to an inner diameter of the test piece tube.

9. The thermo-mechanical analyzer of claim 6, wherein the opening is of a size and shape sufficient to allow the removal of the test piece through the opening.

10. The thermo-mechanical analyzer of claim 6:

wherein the elongate test piece tube defines a long axis;

wherein the opening comprises a slit substantially parallel to the long axis of the test tube piece; and wherein the opening is of a length less than a length of the rigid elongate probe.

11. The thermo-mechanical analyzer of claim 6, wherein the temperature sensor is a thermocouple.

* * * * *